United States Patent [19]

Lindahl et al.

[11] Patent Number: 4,496,550
[45] Date of Patent: Jan. 29, 1985

[54] OLIGOSACCHARIDES HAVING SELECTIVE ANTICOAGULATION ACTIVITY

[75] Inventors: Ulf P. F. Lindahl, Uppsala; Gudrun E. Bäckström, Alunda; John Y. L. Thunberg, Uppsala, all of Sweden

[73] Assignee: KabiVitrum AB, Stockholm, Sweden

[21] Appl. No.: 301,257

[22] Filed: Sep. 11, 1981

[30] Foreign Application Priority Data

Sep. 15, 1980 [SE] Sweden ................. 8006459

[51] Int. Cl.$^3$ ............... A61K 31/725; C08B 37/10
[52] U.S. Cl. .................... 514/54; 536/17.5; 536/21; 514/56
[58] Field of Search ............ 536/21, 18, 17.5; 424/183, 180

[56] References Cited

U.S. PATENT DOCUMENTS

| | | | |
|---|---|---|---|
| 4,281,108 | 7/1981 | Fussi | 536/21 |
| 4,303,651 | 12/1981 | Lindahl et al. | 536/21 |
| 4,401,662 | 8/1983 | Lormeau et al. | 536/21 |
| 4,401,758 | 8/1983 | Lormeau et al. | 536/21 |

FOREIGN PATENT DOCUMENTS

| | | |
|---|---|---|
| 0014184 | 8/1980 | European Pat. Off. . |
| 0027089 | 4/1981 | European Pat. Off. . |
| 2002406 | 2/1979 | United Kingdom . |
| 2035349 | 6/1980 | United Kingdom . |

OTHER PUBLICATIONS

Chem. Abstracts 93:142792d, (1980).
Chem. Abstracts 86:364x, (1977).
Chem. Abstracts 91:85818z, (1979).
Chem. Abstracts 86:67137u, (1977).
Chem. Abstracts 94:44880g, (1981).
Chem. Abstracts 85:89445z, (1976).
Linkler et al, Biochemistry 11(1), 1972, pp. 563–568.
Meyer, Carbohydrate Research, 88(1), 1981, pp. C1–C4.

*Primary Examiner*—Ethel G. Love
*Attorney, Agent, or Firm*—Pollock, Vande Sande & Priddy

[57] ABSTRACT

The invention relates to an oligosaccharide which contains 4-8 monosaccharide units and which is characterized in that it contains at least one glucosamine unit which is 3-0-sulfated, and at least one additional glucosamine unit, whereby these units are linked via an intermediate monosaccharide unit, which is bound to the reducing end of the 3-0-sulfated glucosamine unit. The invention further relates to a pharmaceutical composition containing one or more such oligosaccharides, and to a process for the preparation of these oligosaccharides.

19 Claims, No Drawings

OLIGOSACCHARIDES HAVING SELECTIVE ANTICOAGULATION ACTIVITY

The present invention relates to oligosaccharides which have been shown to possess selective anticoagulation activity, a process for the preparation thereof, and therapeutical compositions containing such oligosaccharides.

Heparin is a sulfate-containing polysaccharide which can be isolated from intestinal mucus from swine or lung from cattle. It is used clinically as an agent for the treatment and prevention of thrombosis. However, the use of heparin is connected with problems, such as risk for bleeding complications and the great individual variation between different patients. Another problem with the present type of heparin therapy is its weak effect on arterial thrombosis. At said type of thrombosis the thrombocyte aggregation is a more dominating feature than at venous thrombosis, where heparin gives a good effect. Standard heparin stimulates to a certain extent thrombocyte aggregation and accordingly gives a negative effect in said respect. It has been shown that heparin fractions of different molecular weights influence the coagulation process in different ways, [L. -O. Andersson et al, Thromb. Res. 9, 575 (1976)]. Coagulation factor X takes a central position in the middle of the coagulation cascade and the inhibition thereof is by many considered especially important to obtain an effective thrombosis-preventing effect [S. Wessler, Thromb. Diath. Haemorrh. 33, 81 (1974)].

According to the present invention it has proved to be possible to obtain oligosaccharides with good selective anticoagulation activity in vivo and in vitro, in particular affinity to antitrombin and capability to improve the capability of reaction of the antithrombin with the coagulation factors X and XII. Animal tests have shown that oligosaccharides of this type give effective preventive effect against thrombosis without any corresponding effect in increase of tendency of bleading. The oligosaccharides according to the invention are characterized in that the sequence of monosaccharides wich compose the oligosaccharide comprise certain monosaccharide units in a certain internal order, as will be defined in the following text.

The invention relates to oligosaccharides, preferably such oligosaccharides that can be derived from heparin, which are characterized in that they exhibit a glucosamine unit, that is 3-O-sulfated, and a further glucosamine unit, whereby these units are connected with an intermediate monosaccharide unit, that is bound to the reducing end of the 3-O-sulfated glucosamine unit. According to one embodiment, the 3-O-sulfated glucosamine unit is also 2-N-sulfated. Furthermore, the additional glucosamine unit, that via an intermediate monosaccharide unit is linked to the reducing end of the 3-O-sulfated glucosamine unit, can be 2-N-sulfated. The intermediate monosaccharide unit is preferably a sulfated iduronic acid unit, wherein the sulfation normally consists of a B 2-O-sulfate group. The invention relates in particular to oligosaccharides, wherein the 3-O-sulfated glucosamine unit is one unit in a sequence of monosaccharide rests with 4, 5, 6, 7 or 8 units of monosaccharide rests.

Oligosaccharides according to the invention, according to any of the preceding definitions can also contain a non-sulfated iduronic acid unit bound in position $C^4$ of the 3-O-sulfated glucosamine unit via 2 intermediate monosaccharide units, whereby preferably one of these intermediate monosaccharide units is an acetylated glucosamine unit, that can be 6-O-sulfated and the other monosaccharide unit preferably is a glucuronic acid unit.

These units can be preceded by one or more additional monosaccharide units, preferably a glucosamine unit, that in turn can be preceded by a uronic acid unit.

Oligosaccharides according to the invention can besides the previously defined monosaccharide units also contain further monosaccharide units, whereby the units which are part of the oligosaccharides preferably are units of uronic acid, such as iduronic and/or glucuronic acid units, interchanging with glucosamine units, The last unit can be a 2,5-anhydro-D-mannose unit, that can be sulfated or non-sulfated.

The 2,5-anhydro-D-mannose unit is preferably introduced at the preparation of the oligosaccharides by cleaving (deaminative cleavage) of a starting material with higher molecular weight.

The oligosaccharides according to the invention can be obtained from natural heparin or possibly be prepared synthetically. When natural heparin is used as starting material the following methods a-e can be used:

(a) treating heparin with nitrous acid in dimethoxy ethane and purifying the material obtained, or (b) treating heparin with nitrite, preferably sodium nitrite, in aqueous solution and purifying the material obtained, or (c) periodate-oxidizing heparin at low pH and temperature, (d) partially depolymerizing heparin with heparinase, or (e) partially depolymerizing heparin by esterification of carboxyl groups and then subjecting the material obtained to alkaline $\beta$-elimination, or (f) partially depolymerizing heparin by partial N-desulfation and thereafter deaminating the material obtained with nitrous acid.

The separation procedure for collecting the highly active components and separating the low active or inactive components can be carried out for example by affinity chromatography on matrix-bound antithrombin III [Höök et al,. FEBS Lett. 66, 90 (1976); Hopwood et al,. FEBS Lett. 69, 51 (1976); L. -O. Andersson et al,. Thromb. Res. 9, 575 (1976)].

The invention also relates to a composition, in particular a pharmaceutical composition, which contains oligosaccharides with selective anticoagulation acitivity, whereby suitably at least 50% or at least 75%, preferably at least 90% and most preferably at least 95% or 99% of the oligosaccharides with anticoagulation activity which are contained in the preparation and which contain a chain of 4 or more monosaccharide units comprise oligosaccharides which fulfil the general definition given above according to the invention, or any of the mentioned specific embodiments of the invention, in particular oligosaccharides according to the invention with 4, 5, 6, 7 or 8 monosaccharide units. These compositions, drugs or pharmaceutical preparations can preferably be in the form of a sterile aqueous solution for injection or as ointment for application via skin or mucous membranes.

The invention also relates to the use of oligosaccharides or of compositions according to the invention in order to counteract or prevent the coagulation of blood in vivo or in vitro, in particular to counteract or prevent thrombosis, particularly arterial thrombosis and/or venous thrombosis.

The invention is further illustrated by the following examples.

EXAMPLE 1. Preparation of heparin fragments by depolymerisation of standard heparin with nitrous acid Heparin (0.5 g) isolated from swine intestines and dissolved in 150 ml of water is chilled to +4° C., and brought to pass through a 3×7 cm column of Dowex ®50 W -28 (H+ form), 200-400 mesh. The column is then washed with 100 ml of water and the washing liquid is combined with the sample. To the sample there are added 250 ml of dimethoxyethane (glyme) chilled to −20° C. and 10 ml of isoamyl nitrite and the mixture, having a temperature of exactly −10° C., is allowed to stand for 35 minutes. The reaction is then discontinued by the addition of 10 ml of 10% Na+-acetate. After addition of 5.2 liters of ethanol, precipitated carbohydrate (heparin derivatives) is recovered by centrifugation. The product is dissolved in 500 ml of 0.05M NaCl-0.05M Tris-HCl, pH 7.4. This solution is divided into 100 ml portions and fractionated by affinity chromatography on a column containing 75 ml of antithrombin-Sepharose ® (Pharmacia Fine Chemicals, Uppsala, Sweden) (about 5 mg of protein per ml gel). The column is eluated by a salt gradient (500 ml of 0.05 NaCl -0.05M Tris-HCl in the mixing vessel; 500 ml of 3M NaCl-0.05M Tris-HCl in the reservoir), the major part of the applied material either passing unretardedly through the column or being eluated at a low ion strength (less than 0.4M NaCl); this material has no biologic activity. The active components (purified oligosaccharide material) are eluated in a wide top 0.5M NaCl and 3M Na Cl corresponding to about 3% of the starting material. These fractions are pooled, concentrated and desalted by gel chromotography.

Oligosaccharides prepared and purified in said manner have a dominating molecular size corresponding to that of an octasaccharide according to the invention.

STUDIES ON ANTICOAGULATION ACTIVITY

The oligosaccharides prepared according to Example 1 were studied in view of their capacity to:
(A) affect the inhibition of the coagulation enzyme thrombin;
(B) affect the inhibition of activated coagulation factor X;
(C) affect the inhibition of activated factor IX;
(D) affect the inhibition of activated factor XI;
(E) affect the inhibition of activated factor XII;
(F) prolong the coagulation time in the blood plasma coagulation test APTT (Activated Partial Thromboplastine Time);
(G) be neutralised by blood plasma components; and
(H) influence the aggregation of thrombocytes.

EXAMPLE A. INHIBITION OF THROMBIN

The capacity of the oligosaccharides to potentiate the inhibition of thrombin with antithrombin III was analysed according to a modification of a method by Teien et al. (Thrombosis Research 11, p. 107–117, 1977). The oligosaccharides were found to have a specific activity of 8 E/mg compared to 120-170 E/mg for standard heparin.

EXAMPLE B. INHIBITION OF ACTIVATED FACTOR X

The capacity of the oligosaccharides to potentiate the inhibition of activated factor X is plasma and in pure antithrombin III was studied according to a modified version of a method by Teien et al. (Thrombosis Research 8, 413, 1976). The oligosaccharides were shown to have a specific activity of 500 E/mg in a pure antithrombin III system and 1900 E/mg in a plasma system compared to 120-170 E/mg for standard heparin.

EXAMPLE C. INHIBITION OF ACTIVATED FACTOR IX

The capacity of the oligosaccharides to potentiate the inhibition of activated factor IX in pure antithrombin III was studied according to Holmer et al. (Biochem. J. 1981. Volume 193 p. 395–400). The oligosaccharides were shown to have a specific activity of 18 E/mg compared to 120-180 E/mg for standard heparin.

EXAMPLE D. INHIBITION OF ACTIVATED FACTOR XI

The capacity of the oligosaccharides to potentiate the inhibition of activated factor XI in pure antithrombin III was studied according to Holmer et al. (Biochem. J. 1981. Volume 193 p. 395–400). The oligosaccharides were shown to have a specific activity of 40 E/mg compared to 120-170 E/mg for standard heparin.

EXAMPLE E. INHIBITION OF ACTIVATED FACTOR XII

The capacity of the oligosaccharides to potentiate the inhibition of activated factor XII in pure antithrombin III was studied according to Holmer et al. (Biochem. J. 1981. Volume 193 p. 395–400). The oligosaccharides were found to have a specific activity of 470 E/mg compared to standard heparin.

EXAMPLE F. PROLONGATION OF THE COAGULATION TIME

The capacity of the oligosaccharides to prolong the coagulation time of blood plasma was studied according to the APTT (Activated Partial Thromboplastine Time) method [Andersson et al,. Thromb. Res. 9 575 (1976)]. The oligosaccharides showed a specific activity of 12 E/mg compared to 3rd International Heparin Standard. Standard heparin shows a specific activity in the range 120-170 E/mg.

EXAMPLE G. NEUTRALISATION OF THE OLIGOSACCHARIDES IN BLOOD PLASMA

The neutralising effect on the oligosaccharides by plasma components was studied by measuring the effect of heparin and of the oligosaccharides in plasma and in a pure antithrombin system. This was performed by measuring the amount of activated factor X inhibited in the two systems in the presence of a certain amount of heparin or oligosaccharide. The activity of the oligosaccharides showed a 18% neutralisation by plasma components, while the corresponding figure of standard heparin was shown to be 75%.

EXAMPLE H. THROMBOCYTE INFLUENCE

The capacity of the oligosaccharides to aggregate thrombocytes at critical ADP (Adenosine DiPhosphate)-concentrations was studied substantially according to Beck, E. A. (Thromb Haem Stuttg. 1977, 38, 578). It was shown that the thrombocyteaggregating capacity of the oligosaccharides was ten times lower than that of standard heparin, calculated by weight.

We claim:

1. Oligosaccharide comprising 4–8 monosaccharide units, characterized in that it contains at least one glucosamine unit which is 3-O-sulfated, and at least one further glucosamine unit, whereby these units are connected by an iduronic unit linking monosaccharide unit, which is bound to the reducing end of the 3-O-sulfated glucosamine unit.

2. Oligosaccharide according to claim 1, characterized in that the 3-O-sulfated glucosamine unit also is 2-N-sulfated.

3. Oligosaccharide according to claim 1 or claim 2, characterized in that the said at least one further glucosamine unit is 2-N-sulfated.

4. Oligosaccharide according to claim 1, characterized in that the intermediate monosaccharide unit is a sulfated iduronic acid unit.

5. Oligosaccharide according to claim 1, characterized in that it contains a non-sulfated iduronic acid unit linked to position $C^4$ of the 3-O-sulfated glucosamine unit via two linking monosaccharide units.

6. Oligosaccharide according to claim 1, characterized in that its last unit is a 2,5-anhydro-D-mannose unit, which can be sulfated or non-sulfated.

7. Oligosaccharide according to claim 1, characterized in that it exhibits selective coagulation activity by affinity to antithrombine and increases the reactivity of antithrombine towards factor X.

8. Oligosaccharide according to claim 1, characterized in that it is a tetrasaccharide, pentasaccharide, hexasaccharide, heptasaccharide or an octasaccharide.

9. A pharmaceutical preparation, characterized in that it contains one or more oligosaccharides according to claim 1 in an amount sufficient for anticoagulation activity.

10. The oligosaccharide of claim 5 wherein one of the two linking monosaccharide units is an acetylated glucosamine unit, and the other of the two linking monosaccharide units is a glucuronic acid unit.

11. The oligosaccharide of claim 10 wherein said acetylated glucosamine unit is 6-O-sulfated.

12. Oligosaccharide according to claim 11 characterized in that its last unit is a 2,5-anhydro-D-mannose unit, which can be sulfated or non-sulfated.

13. The oligosaccharide of claim 12 wherein said 2,5-anhydro-D-mannose unit is sulfated.

14. Oligosaccharide according to claim 2 characterized in that the intermediate monosaccharide unit is a sulfated iduronic acid unit.

15. Oligosaccharide according to claim 14 characterized in that the said at least one further glucosamine unit is 2-N-sulfated.

16. Oligosaccharide according to claim 15 characterized in that it contains a non-sulfated iduronic acid unit linked to position $C^4$ of the 3-O-sulfated glucosamine unit via two linking monosaccharide units.

17. Oligosaccharide according to claim 16 wherein one of the two linking monosaccharide units is an acetylated glucosamine unit and the other of the two linking monosaccharide units is a glucuronic acid unit.

18. Oligosaccharide according to claim 17 wherein said acetylated glucosamine unit is 6-O-sulfated.

19. Oligosaccharide according to claim 18 characterized in that its last unit is a 2,5-anhydro-D-mannose unit, which can be sulfated or non-sulfated.

* * * * *